US011617753B2

(12) United States Patent
Smith et al.

(10) Patent No.: US 11,617,753 B2
(45) Date of Patent: Apr. 4, 2023

(54) METHODS OF TREATING AND INHIBITING EBOLA VIRUS INFECTION

(71) Applicants: OYAGEN, INC., Rochester, NY (US); The United States of America, as represented by the Secretary of Health and Human Services, Bethesda, MD (US)

(72) Inventors: Harold C. Smith, Rochester, NY (US); Ryan P. Bennett, Clifton Springs, NY (US); Peter Jahrling, Bend, OR (US)

(73) Assignees: OYAGEN, INC., Rochester, NY (US); The United States of America, as represented by the Secretary of Health and Human Services, Bethesda, MD (US)

( * ) Notice: Subject to any disclaimer, the term of this patent is extended or adjusted under 35 U.S.C. 154(b) by 0 days.

(21) Appl. No.: 16/348,867

(22) PCT Filed: Nov. 6, 2017

(86) PCT No.: PCT/US2017/060207
§ 371 (c)(1),
(2) Date: May 9, 2019

(87) PCT Pub. No.: WO2018/098306
PCT Pub. Date: May 17, 2018

(65) Prior Publication Data
US 2020/0188404 A1    Jun. 18, 2020

Related U.S. Application Data

(60) Provisional application No. 62/420,474, filed on Nov. 10, 2016.

(51) Int. Cl.
*A61K 31/52* (2006.01)
*A61K 31/7064* (2006.01)

(52) U.S. Cl.
CPC .......... *A61K 31/52* (2013.01); *A61K 31/7064* (2013.01)

(58) Field of Classification Search
CPC .. A61K 31/519; A61K 31/7064; A61K 31/52; A61P 31/12; A61P 31/14; A61P 1/16
See application file for complete search history.

(56) References Cited

U.S. PATENT DOCUMENTS

| | | | |
|---|---|---|---|
| 3,423,398 A | 1/1969 | Rao | |
| 6,232,282 B1 | 5/2001 | Kvietok | |
| 6,335,339 B1* | 1/2002 | Arenas | A61K 31/53 514/241 |
| 7,125,855 B2 | 10/2006 | Bhat | |
| 7,442,185 B2 | 10/2008 | Amark | |
| 8,038,649 B2 | 10/2011 | Kronestedt | |
| 8,062,255 B2 | 11/2011 | Brunnberg | |
| 8,075,517 B2 | 12/2011 | Karlsson | |
| 8,235,952 B2 | 8/2012 | Wikner | |
| 8,277,412 B2 | 10/2012 | Kronestedt | |
| 8,440,813 B2 | 5/2013 | Babu | |
| 8,475,804 B2 | 7/2013 | Johansen | |
| 8,529,510 B2 | 9/2013 | Giambattista | |
| 8,551,054 B2 | 10/2013 | Guillermo | |
| 9,724,360 B2 | 8/2017 | Chun | |
| 9,949,994 B2 | 4/2018 | Chun | |
| 10,479,996 B2 | 11/2019 | Iversen | |
| 10,548,971 B2 | 2/2020 | Weiner | |
| 2004/0259934 A1 | 12/2004 | Olsen | |
| 2010/0087388 A1* | 4/2010 | Kotra | A61P 31/04 514/51 |
| 2010/0172917 A1 | 7/2010 | Ter Meulen | |
| 2010/0233250 A1 | 9/2010 | Baras | |
| 2011/0028564 A1* | 2/2011 | Johansen | A61K 31/5415 514/657 |
| 2011/0218210 A1 | 9/2011 | Refaeli | |
| 2012/0014911 A1 | 1/2012 | Fuchs | |
| 2016/0122374 A1 | 5/2016 | Chun | |
| 2016/0361330 A1 | 12/2016 | Chun | |
| 2017/0165230 A1 | 6/2017 | Rudd | |
| 2019/0255085 A1 | 8/2019 | Clarke | |
| 2019/0275063 A1 | 9/2019 | Chun | |
| 2019/0351048 A1 | 11/2019 | Rauch | |
| 2020/0017514 A1 | 1/2020 | Plewe | |
| 2021/0236497 A1 | 8/2021 | Smith | |

FOREIGN PATENT DOCUMENTS

| | | |
|---|---|---|
| WO | WO2005020885 | 3/2005 |
| WO | WO2009067409 | 5/2009 |
| WO | WO2002057287 | 7/2009 |
| WO | WO2016069826 | 5/2016 |
| WO | WO2016069827 | 5/2016 |
| WO | WO2018089306 | 5/2018 |

(Continued)

OTHER PUBLICATIONS

Panchal et. al., J. Biomolecular Screening, 2010, Soc. Laboratory Automation & Screening, vol. 15(7), pp. 755-765 (Year: 2010).*
Hinshaw et. al., The J. Organic Chem., 1970, vol. 35(1), pp. 236-241 (Year: 1970).*
Krawczyk et. al., J. Med. Chem., 1995, vol. 38, pp. 4115-4119 (Year: 1995).*
Corman et al., "Detection of 2019 novel coronavirus (2019-nCoV) by real-time RT-PCR," Euro Surveillance, 25(30:2000045 (2020).
Dyall et al., "Discovery of Inhibitors of Middle East Respiratory Syndrome Coronavirus Infection" International Conference on Antimicrobial Research, Madrid Spain, Oct. 2014 (see abstract 41, p. 55).

(Continued)

*Primary Examiner* — Sarah Pihonak (74) *Attorney, Agent, or Firm* — Haley Guiliano LLP; James F. Haley, Jr.; Mihaela D. Danca (57) ABSTRACT

Disclosed herein are methods for treating an Ebola virus and inhibiting the transmission and propagation thereof.

4 Claims, 8 Drawing Sheets

(56) References Cited

FOREIGN PATENT DOCUMENTS

| WO | WO2019018185 | 1/2019 |
|---|---|---|
| WO | WO2019079339 | 4/2019 |

OTHER PUBLICATIONS

Hardesty et al., "The disposition of the antitumor agent, sangivamycin, in mice," Cancer Research, 34(5):005-1009 (1974).
Ji et al., "SARS-CoV proteins decrease levels and activity of human ENaC via activation of distinct PKC isoforms," American Journal of Physiology. Lung Cellular and Molecular Physiology, 296(3):L372-83 (2009).
Kucic et al., "Inhibition of protein kinases C prevents murine cytomegalovirus replication," Journal of General Virology, 86(Pt 8):2153-2161 (2005).
Vittori et al., "Antiviral properties of deazaadenine nucleoside derivatives," Current Medical Chemistry, 13(29):3529-3552 (2006).
Wang et al., "Remdesivir and chloroquine effectively inhibit the recently emerged novel coronavirus (2019-nCoV) in vitrom," Cell Research, 30(3):269-271 (2020).
U.S. Appl. No. 16/851,047, filed Apr. 16, 2020, Harold C. Smith.
Dolloff et al., "Sangivamycin-like Molecule 6 Exhibits Potent Anti-Multiple Myeloma Activity through Inhibition of Cyclin-Dependent Kinase-9," Molecular Cancer Therapies, 11(11)L:2321-2330 (2012).
PubChem, "4-Amino-7-[(2R,3S,4S,5R)-3,4-dihydroxy-5-(hydroxymethyl)oxolan-2-yl]-6-hydrazinylpyrrolo[2,3-d]pyrimidine-5-carboxamide," dated Nov. 9, 2021 (13 pages).
Cavins et al., "Initial toxicity study of sangivamycin (NSC-65346)," Cancer Chemotherapy Reports, 51(4):197-200 (1967).

* cited by examiner

METHODS OF TREATING AND INHIBITING EBOLA VIRUS INFECTION

CROSS REFERENCE TO RELATED APPLICATIONS

This application is a U.S. National Phase filing under 35 U.S.C. § 371 of International Application No. PCT/US2017/060207, filed Nov. 6, 2017, and published as WO 2018/089306 A1 on May 17, 2018, which claims priority benefit of U.S. Provisional Patent Application Ser. No. 62/420,474, filed Nov. 10, 2016, the disclosures of which are hereby incorporated by reference herein in their entirety.

STATEMENT REGARDING FEDERALLY FUNDED RESEARCH

This discovery was made with government support by the Department of Health and Human Services. The government has certain rights in the invention.

FIELD OF THE DISCLOSURE

Disclosed herein are methods for treating an Ebola virus and inhibiting the transmission and propagation thereof.

BRIEF DESCRIPTION OF THE FIGURES

FIGS. 1A-1D are micrographs depicting the EGFP fluorescence and Hoechst 33342 nuclear DNA stains of wild type Ebola virus and the L117R Ebola virus mutation. FIGS. 1A and 1B indicate the wild type virus can dimerize, hence, form the hexamers which led to the formation of the viral capsid. FIGS. 1C and 1D demonstrate that the L117R mutation prevents dimerization resulting in the inability of the mutated virus to form virus-like particles (VLPs) on the plasma membrane, i.e., the fluorescent rings around the edges of cells.

FIGS. 2A-2F indicate the wild type virus can dimerized, hence, form the hexamers which led to the formation of the viral capsid.

FIG. 4 lane 4 represents 12 µL of VLP isolated from mutated L117R VP40 expressing cells, indicating a lack of VLP formation.

FIGS. 5A and 5B show similar amounts of VLP, while FIG. 5C shows a clear reduction in VLP at 50 nM sangivamycin. FIG. 5D shows a drastic reduction in VLP at 500 nM sangivamycin with VLP only faintly detected at 12 µL in lane 3.

FIGS. 7A-7F are graphs summarizing in vitro cell-based antiviral assays. The percent inhibition that the test compounds displayed is indicated by (●), whereas the percent toxicity is indicated by (■). These assays were used to evaluate the antiviral capability of the disclosed compounds against a fully-functional Ebola virus.

DETAILED DESCRIPTION OF THE DISCLOSURE

The materials, compounds, compositions, articles, and methods described herein may be understood more readily by reference to the following detailed description of specific aspects of the disclosed subject matter and the Examples included therein.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

The terms "a" and "an" are defined as one or more unless this disclosure explicitly requires otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the disclosed methods or compositions can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Any embodiment of any of the disclosed compounds or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

As used herein, the term "subject" refers to a human or an animal that has been diagnosed with one or more strains of Ebola virus or has tested positive for Ebola virus. The term subject also includes humans or animals that have been exposed to Ebola virus but are not symptomatic.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like are encompassed within the term "treating," and refer to reducing the probability of developing a disorder or condition in a subject, who does not have, but is at risk of or susceptible to developing a disorder or condition.

As used herein, "pharmaceutically acceptable" means physiologically tolerable, for either human or veterinary applications. In addition, "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. Essentially, the pharmaceutically acceptable material is nontoxic to the recipient. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

"Test agents" or otherwise "test compounds" as used herein refers to an agent or compound that is to be screened in one or more of the assays described herein. Test agents include compounds of a variety of general types including, but not limited to, small organic molecules, known pharmaceuticals, polypeptides; carbohydrates such as oligosaccharides and polysaccharides; polynucleotides; lipids or phospholipids; fatty acids; steroids; or amino acid analogs. Test agents can be obtained from libraries, such as natural product libraries and combinatorial libraries. In addition, methods of automating assays are known that permit screening of several thousands of compounds in a short period.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with which the publications are cited.

Details associated with the embodiments described above and others are described below.

Methods

Disclosed herein are methods for treating a subject having an Ebola virus infection. One aspect of the disclosure comprises, contacting the subject with a therapeutically effective amount of one or more compounds having Formula I:

Formula I wherein X is chosen from O or S;
$R^1$ is chosen from —$NH_2$, —NHOH and —$NHNH_2$; and
$R^2$ is chosen from hydrogen and —$NHNH_2$; or
a pharmaceutically acceptable salt thereof.

The disclosed compounds can be used to treat, cure, abate, minimize, control, and/or lessen the effects of Ebola virus in humans and animals. The disclosed compounds can also be used to slow the rate of Ebola virus spread in a population. The disclosed compounds when administered to a subject in need of treatment can be used to stop the spread of Ebola virus. As such, the compounds disclosed herein can be administered as part of a combination therapy with one or more drugs or other pharmaceutical agents.

Disclosed herein are methods for preventing the spread of Ebola virus. The methods comprise administering an effective amount of one or more of the disclosed compounds to a subject diagnosed or exposed to one or more Ebola viruses.

Further disclosed herein is the use of the disclosed compounds for making a medicament useful in treating a subject infected with one or more Ebola viruses.

As indicated in Formula I all enantiomers and diastereomers of Formula I are included as compounds suitable for use in the herein disclosed methods for treating a subject infected with an Ebola virus. Non-limiting examples of Ebola viruses include Ivory Coast Ebola virus (ICEBOV), Zaire Ebola virus (ZEBOV), and Sudan Ebola Virus (SEBOV).

VP40 Inhibition

Without wishing to be limited by theory, the disclosed compounds inhibit Ebola VP40 protein. Ebola VP40 protein localizes to the inner leaflet of the plasma membrane of human cells where it provides an essential function in guiding the formation of new viral particles and is part of the viral particle. VP40's homodimer is a cytoplasmic protein that is an essential building block for the homo octomer formation (ring structure) in the early viral life cycle that regulates transcription and nuclear import; while a linear homo hexamer formation in the late viral life cycle regulates viral particle assembly at the inner plasma membrane of the cell. The disclosed compounds inhibit Ebola VP40 protein, thereby impairing the assembly of infectious viral particles of the Ebola virus. This results in keeping the Ebola virus from the formation of particles that can exit the host cell, thereby truncating the virulence of Ebola viruses.

Therefore, disclosed herein are methods for inhibiting the self-assembly of Ebola VP40 protein in a cell, comprising contacting a cell in vitro, ex vitro or in vivo that is infected with one or more Ebola viruses with one or more compounds of Formula (I). As it relates to the disclosed methods for inhibiting the self-assembly of Ebola VP40 protein in vivo, this method includes treatment of all mammals, especially treatment of humans.

Further disclosed herein is the use of the disclosed compounds for making a medicament inhibiting the self-assembly of Ebola VP40 protein in a subject infected with one or more strains of Ebola virus, thereby inhibiting the Ebola virus from forming and releasing virus particles that would otherwise exit the infected cell and spread the infection.

One embodiment of this aspect of the disclosure relates to methods for treating a subject having an Ebola virus infection, comprising contacting the subject with a therapeutically effective amount of one or more compounds of Formula II:

Formula II wherein X, $R^1$ and $R^2$ are the same as disclosed herein above; or a pharmaceutically acceptable salt thereof.

One example of this embodiment comprises, contacting a subject having an Ebola virus infection with a therapeutically effective amount of 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide (sangivamycin) having Formula IIIa:

Formula IIIa or a pharmaceutically acceptable salt thereof. This compound is available from Sigma-Aldrich™.

A further example of this embodiment comprises, contacting a subject having an Ebola virus infection with a therapeutically effective amount of 4-amino-7-((2R,3R,4S,5R)-3,4-dihydroxy-5-(hydroxymethyl)tetrahydrofuran-2-yl)-6-hydrazinyl-N-hydroxy-7H-pyrrolo[2,3-d]pyrimidine-5-carboximidamide having Formula IIIb:

Formula IIIb or a pharmaceutically acceptable salt thereof. This compound is referred to in the literature as 'Sangivamycin-Like Molecule 5 (SLM5) and is available from the NIH Developmental Therapeutics Program (DTP).

Another example of this embodiment comprises, contacting a subject having an Ebola virus infection with a therapeutically effective amount of 4-amino-7-((2R,3R,4S,5R)-3,4-dihydroxy-5-(hydroxymethyl)tetrahydrofuran-2-yl)-6-hydrazinyl-7H-pyrrolo[2,3-d]pyrimidine-5-carboximidhydrazide having Formula IIIc:

Formula IIIc or a pharmaceutically acceptable salt thereof. This compound is referred to in the literature as 'Sangivamycin-Like Molecule 6 (SLM6) and is available from the NIH Developmental Therapeutics Program (DTP).

A still further example of this embodiment comprises, contacting a subject having an Ebola virus infection with a therapeutically effective amount of 4-amino-7-((2R,3R,4S,5R)-3,4-dihydroxy-5-(hydroxymethyl)tetrahydrofuran-2-yl)-6-hydrazinyl-7H-pyrrolo[2,3-d] pyrimidine-5-carboximidamide having Formula IIId:

Formula IIId or a pharmaceutically acceptable salt thereof. This compound is referred to in the literature as 'Sangivamycin-Like Molecule 7 (SLM7) and is available from the NIH Developmental Therapeutics Program (DTP).

A yet further example of this embodiment comprises, contacting a subject having an Ebola virus infection with a therapeutically effective amount of 4-amino-7-((2R,3R,4S,5R)-3,4-dihydroxy-5-(hydroxymethyl)tetrahydrofuran-2-yl)-7H-pyrrolo[2,3-d]pyrimidine-5-carbothioamide (thiosangivamycin) having Formula IIIe:

Formula IIIe or a pharmaceutically acceptable salt thereof.

Further disclosed is a method for inhibiting in a subject infected with one or more Ebola viruses, the self-assembly of Ebola VP40 protein, the method comprising contacting the infected subject with a therapeutically effective amount of a compound chosen from:

or a pharmaceutically acceptable salt thereof.

RNA Polymerase Inhibition

Further disclosed herein are methods for inhibiting the activity of the Ebola RNA dependent RNA polymerase (interchangeably referred to herein as the L polymerase or the L protein). Without wishing to be limited by theory the Ebola virus activity is inhibited by inhibiting L protein (RNA polymerase) activity, which in turn inhibits viral genome replication and the production of the Ebola virus.

Therefore, disclosed herein are methods for treating a subject infected by an Ebola virus by inhibiting the activity of the Ebola viral RNA polymerase. This method comprises, contacting a subject infected with an Ebola virus with a therapeutically effective amount of one or more compounds having Formula I or a pharmaceutically acceptable salt thereof.

Further disclosed herein is the use of the disclosed compounds for making a medicament inhibiting the activity of Ebola viral RNA polymerase in a subject infected with one or more strains of Ebola virus, thereby inhibiting the Ebola virus from forming viral particles that would otherwise exit the infected cell and spread the infection.

One embodiment of the methods for inhibiting Ebola virus RNA polymerase in a subject infected with an Ebola virus comprises, contacting the subject with a therapeutically effective amount of one or more compounds of Formula II:

Formula II wherein X, $R^1$ and $R^2$ are the same as disclosed herein above; or a pharmaceutically acceptable salt thereof.

One example of this embodiment comprises, contacting a subject having an Ebola virus infection with a therapeutically effective amount of 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide (sangivamycin) having Formula IIIa:

Formula IIIa or a pharmaceutically acceptable salt thereof.

Another example of this embodiment comprises, contacting a subject having an Ebola virus infection with a therapeutically effective amount of 4-amino-7-((2R,3R,4S,5R)-3,4-dihydroxy-5-(hydroxymethyl)tetrahydrofuran-2-yl)-6-hydrazinyl-N-hydroxy-7H-pyrrolo[2,3-d]pyrimidine-5-carboximidamide having Formula IIIb:

Formula IIIb or a pharmaceutically acceptable salt thereof.

A further example of this embodiment comprises, contacting a subject having an Ebola virus infection with a therapeutically effective amount of 4-amino-7-((2R,3R,4S,5R)-3,4-dihydroxy-5-(hydroxymethyl)tetrahydrofuran-2-yl)-6-hydrazinyl-7H-pyrrolo[2,3-d]pyrimidine-5-carboximidhydrazide having the Formula IIIc:

Formula IIIc or a pharmaceutically acceptable salt thereof.

A still further example of this embodiment comprises, contacting a subject having an Ebola virus infection with a therapeutically effective amount of 4-amino-7-((2R,3R,4S,5R)-3,4-dihydroxy-5-(hydroxymethyl)tetrahydrofuran-2-yl)-6-hydrazinyl-7H-pyrrolo[2,3-d] pyrimidine-5-carboximidamide having Formula IIId:

Formula IIId or a pharmaceutically acceptable salt thereof.

A yet further example of this embodiment comprises, contacting a subject having an Ebola virus infection with a therapeutically effective amount of 4-amino-7-((2R,3R,4S, 5R)-3,4-dihydroxy-5-(hydroxymethyl)tetrahydrofuran-2-yl)-7H-pyrrolo[2,3-d]pyrimidine-5-carbothioamide (thio-sangivamycin) having Formula IIIe:

Formula IIIe or a pharmaceutically acceptable salt thereof.

Without wishing to be limited by theory, the disclosed compounds can be used to treat an Ebola virus by inhibiting the activity of RNA polymerase and for infected cells wherein the virus has replicated prior to treatment, inhibits the release of Ebola viruses from the infected cell by inhibiting VP40 self-assembly.

Prodrugs

Further disclosed herein are methods for treating a subject having an Ebola virus infection with the disclosed compounds, wherein the disclosed compounds serve as prodrugs which form an active pharmaceutical ingredient (API) once inside cells, tissues and following contact with the human body. Without wishing to be limited by theory, the disclosed compounds can form a triphosphate analog which when formed in the cell can bind to VP40 to prevent multimerization or be incorporated into the RNA by viral RNA-dependent RNA polymerases or DNA-dependent RNA polymerases or DNA-dependent DNA polymerases and thereby stop replication of the virus by preventing appropriate replication of the viral genetic material and prevent viral gene expression.

As such, one aspect of the disclosure comprises, contacting the subject with a therapeutically effective amount of one or more compounds having Formula II, as shown above, that are converted in vivo to the corresponding triphosphate having Formula V:

wherein X, R¹ and R² are the same as disclosed herein above.

The following is a non-limiting example of an API formed in vivo from the disclosed compound sangivamycin:

This API and the corresponding triphosphates of the other disclosed compounds can be readily prepared by enzymatic methods known in the art for the preparation of adenosine triphosphate.

Therefore, further disclosed herein is a method for treating a subject having an Ebola virus, comprising contacting the subject with a compound having the formula:

wherein X is chosen from O or S;
R¹ is chosen from —NH₂, —NHOH and —NHNH₂; and
R² is chosen from hydrogen and —NHNH₂.

As such, disclosed herein is the use of the disclosed compounds for preventing VP40 protein self-assembly of Ebola viruses thereby eliminating the ability of the virus to form a viral capsid. Also disclosed herein is the use of the disclosed compounds to inhibit the activity of Ebola virus RNA polymerase thereby inhibiting the Ebola virus from replicating in an infected cell.

Compositions

Compositions suitable for delivery of the disclosed compounds include aqueous-based compositions. The compositions can be delivered intramuscularly or intravenously. The amount of the disclosed compounds delivered to a subject in a single treatment (also referred to herein as a "bolus") can be determined by the person providing the treatment. In general, amounts up to 50 mg/kg can be delivered in a single treatment whether IM or IV.

The disclosed single dose compositions can comprise any amount of the disclosed compounds from about 0.5 mg/kg to about 50 mg/kg, for example, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, or 50 mg/kg.

As such, the compositions useful for providing a medicament for inhibiting Ebola virus transmission can comprise from about 0.5 mg/kg to about 50 mg/kg of the subject's body mass. Therefore, a single dose of the disclosed compounds can range from about 0.5 mg/kg to about 50 mg/kg of the subject's body mass. In one embodiment, the amount of compound in a single dose is from about 1 mg/kg to about 25 mg/kg of the subject's body mass. In another embodiment, the amount of compound in a single dose is from about 10 mg/kg to about 25 mg/kg of the subject's body mass. In a further embodiment, the amount of compound in a single dose is from about 15 mg/kg to about 25 mg/kg of the subject's body mass. In a yet further embodiment, the amount of compound in a single dose is from about 1 mg/kg to about 10 mg/kg of the subject's body mass. In a still further embodiment, the amount of compound in a single dose is from about 5 mg/kg to about 20 mg/kg of the subject's body mass.

Therefore, disclosed herein are pharmaceutical compositions suitable for a single dose administration, comprising:
a) from about 0.5 mg/kg to about 50 mg/kg of the subject to be treated; and
b) the balance a pharmaceutically acceptable carrier.

Controls

Figure 1A:
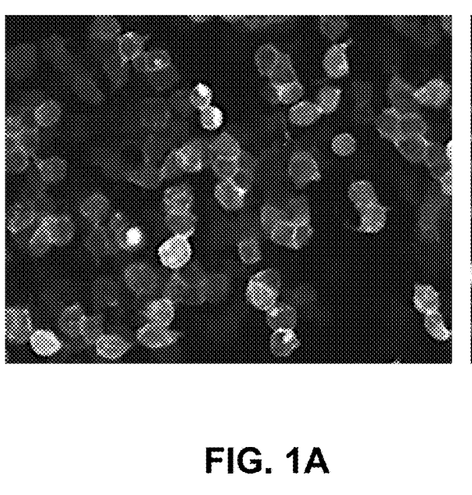
FIG. 1A is an image depicting EGFP fluorescence from the VP40 protein tagged with EGFP of the VP40 from wild type Ebola virus.
Figure 1B:
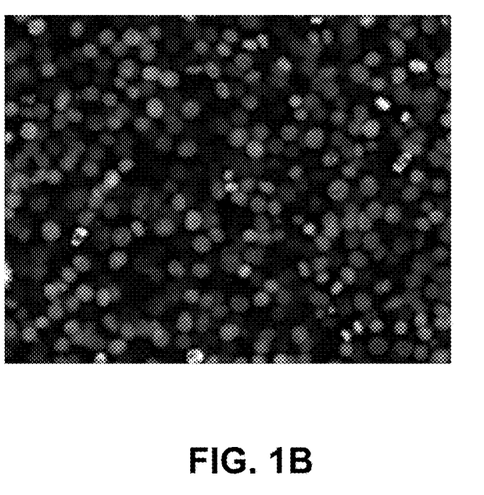
FIG. 1B is the corresponding Hoechst 33342 DNA stain.
Figure 1C:
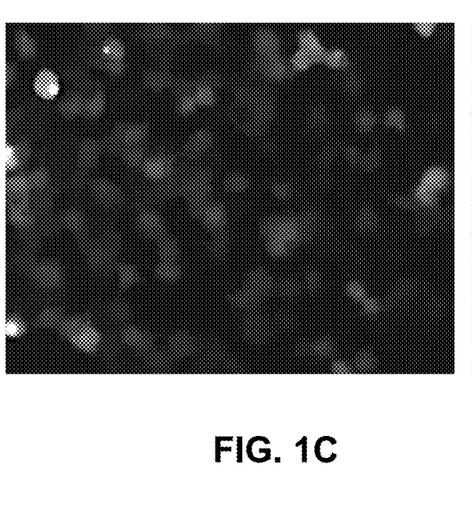
Figure 1D:
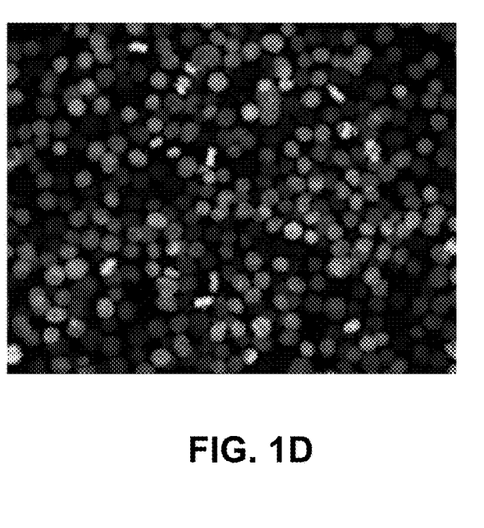

FIGS. 1A-1D are micrographs depicting the EGFP fluorescence and Hoechst 33342 nuclear DNA stains of wild type Ebola virus and the L117R Ebola virus mutation. FIG. 1A is an image depicting EGFP fluorescence from the VP40 protein tagged with EGFP of the VP40 dimer in wild type Ebola virus. FIG. 1B is the corresponding Hoechst 33342 DNA stain. FIGS. 1A and 1B indicate the wild type virus can dimerized, hence, form the hexamers which led to the formation of the viral capsid. FIGS. 1C and 1D demonstrate that the L117R mutation prevents dimerization resulting in the inability of the mutated virus to form virus-like particles (VLPs) on the plasma membrane, i.e., the fluorescent rings around the edges of cells.

EXAMPLE 1

293T cells were plated at 10,000 cells/well in 384-well format and transfected with EGFP-V5-VP40. After 4 hours the cells were treated with a range of concentrations of compound (600-2.34 nM). 16 hours after drug was added fluorescence was read (ex. 485/em. 535) on a Biotek Synergy4 plate reader and cells were fixed in 4% paraformaldehyde with Hoechst 33342 and washed with PBS for imaging.

Figure 2A:
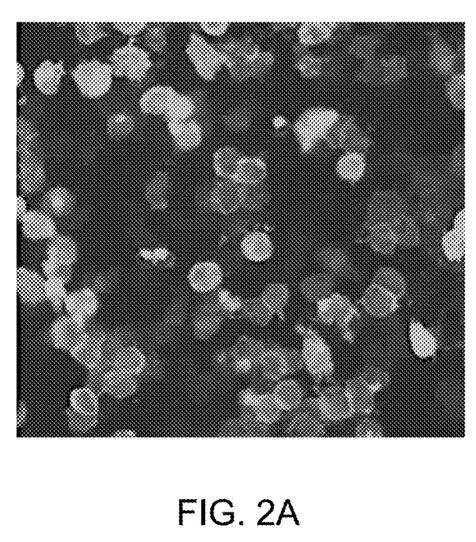
FIG. 2A-2F are micrographs of Ebola virus treated with 2.34 nM, 9.38 nM and 37.5 nM sangivamycin, respectively.
Figure 2B:
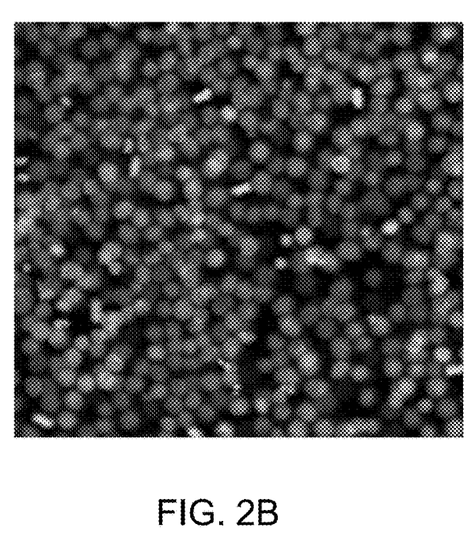
Figure 2C:
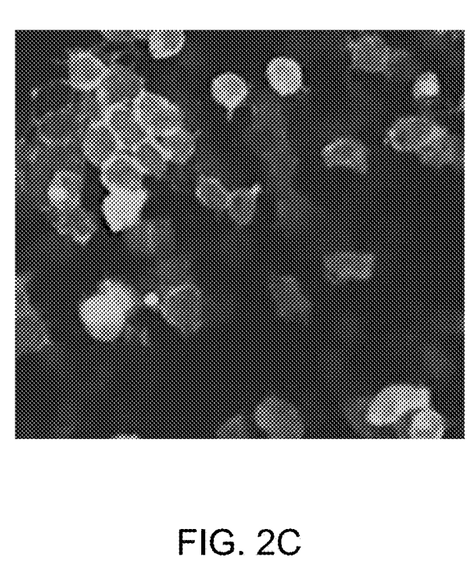
Figure 2D:
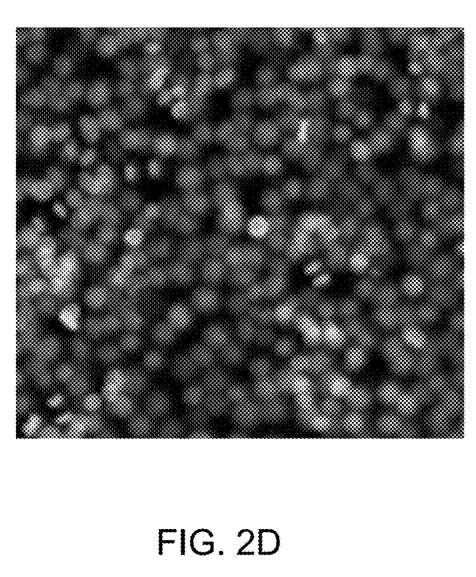
Figure 2E:
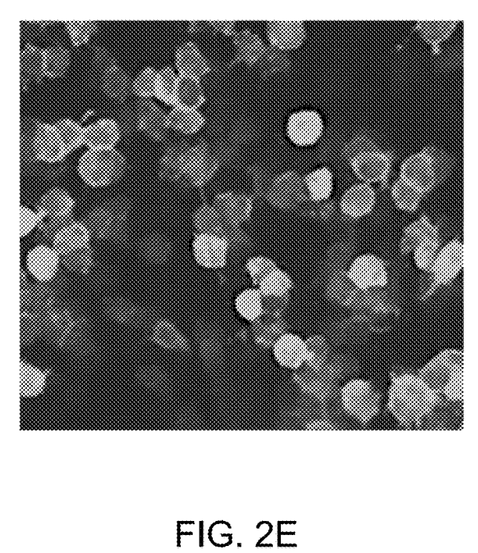
Figure 2F:
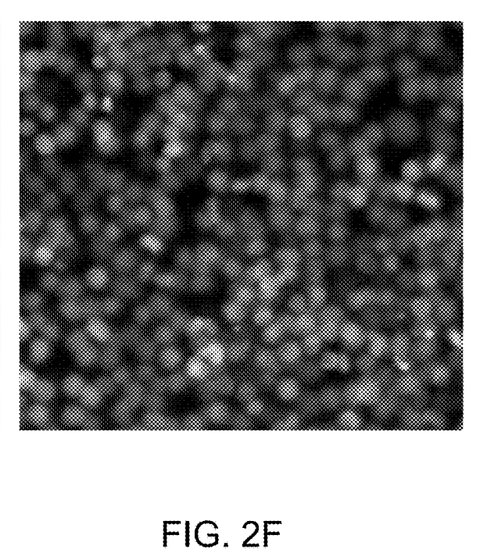
Figure 2G:
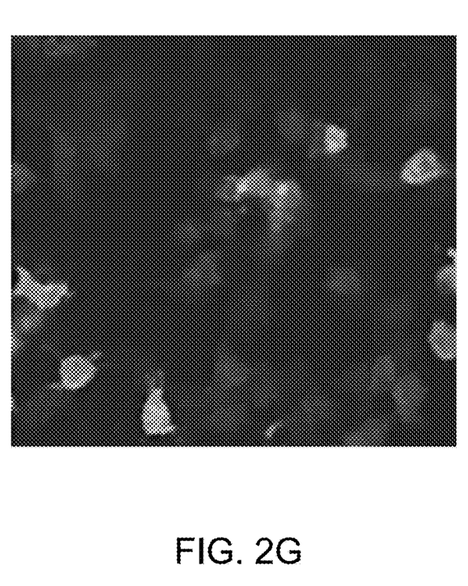
FIGS. 2G-2J show a shift in membrane association as depicted in a L117R Ebola virus mutation shown in FIG. 1C at 150 nM (FIG. 2G) and 600 nM (FIG. 2I), revealing that at concentrations above 37.5 nM sangivamycin prevents VLP formation in the cell.
Figure 2H:
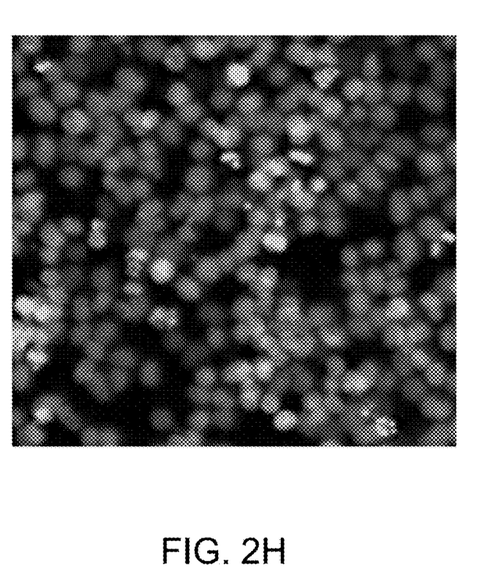
Figure 2I:
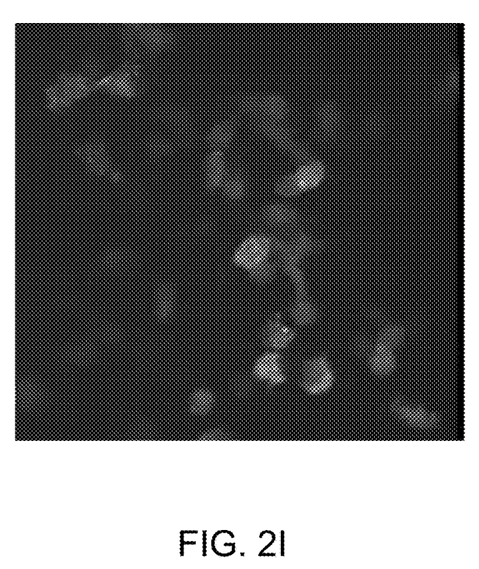
Figure 2J:
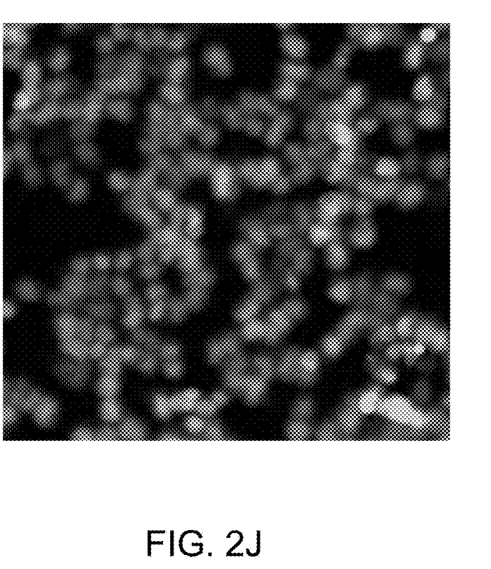

FIG. 2A-2J demonstrate that sangivamycin causes a shift in membrane associated VP40. FIG. 2A depicts the EGFP fluorescence of VP40 from wild type Ebola virus that has been treated with 2.34 nM of sangivamycin. FIG. 2B is the corresponding Hoechst 33342 DNA stain image. FIG. 2C depicts the EGFP fluorescence of VP40 from wild type Ebola virus that has been treated with 9.38 nM of sangivamycin. FIG. 2D is the corresponding Hoechst 33342 DNA stain image. FIG. 2E depicts the EGFP fluorescence of VP40 in wild type Ebola virus that has been treated with 37.5 nM of sangivamycin. FIG. 2F is the corresponding Hoechst 33342 DNA stain image. FIGS. 2A-2F indicate the wild type virus can dimerized, hence, form the hexamers which led to the formation of the viral capsid. FIGS. 2G-2J show a shift in membrane association as depicted with the L117R mutation in FIG. 1C at 150 nM (FIG. 2G) and 600 nM (FIG. 2I), revealing that at concentrations above 37.5 nM sangivamycin prevents VLP formation in the cell.

Figure 3:
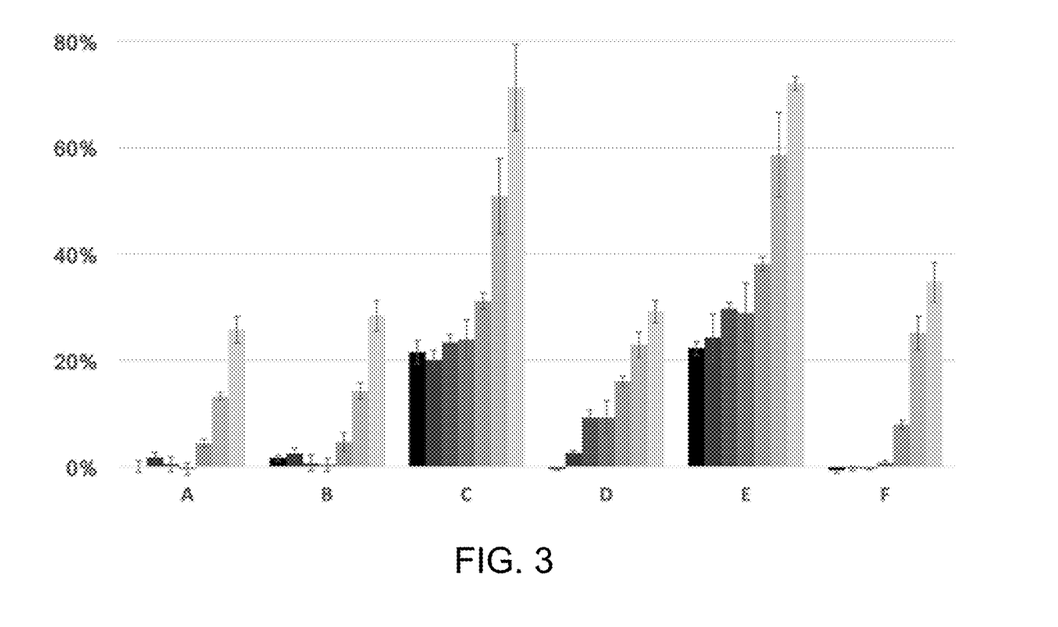
FIG. 3 is a series of histograms that represent the reduced fluorescence (expressed as % of solvent control signal) of EGFP tagged VP40 proteins expressed in cells treated with the disclosed compounds at varying concentrations. For each compound, i.e., A-F the doses are in each histogram from left to right 30 µM, 15 µM, 7.5 µM, 3.75 µM, 1.88 µM, 0.94 µM, and 0.46 µM respectively. Histogram A represents sangivamycin, B represents sangivamycin HCl salt and F represents thiosangivamycin. Histograms C-E represent Formulae IIIb-IIId disclosed herein.

The lack of VLP formation lowers the overall fluorescence in cells expressing VP40 and reading EGFP fluorescence signal in cells with increasing concentrations of compound is another indication of inhibition of VLP through VP40. FIG. 3 depicts a series of bar graphs for samples labeled A-F. The compounds from A-F are as follows:

A) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide (sangivamycin) having Formula IIIa (NSC #65346);

B) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide (sangivamycin) hydrochloride, HCl salt of Formula IIIa (NSC #143648);

C) 4-amino-7-((2R,3R,4S,5R)-3,4-dihydroxy-5-(hydroxymethyl)tetrahydrofuran-2-yl)-6-hydrazinyl-N-hydroxy-7H-pyrrolo[2,3-d]pyrimidine-5-carboximidamide having Formula IIIb (NSC #107517);

D) 4-amino-7-((2R,3R,4S,5R)-3,4-dihydroxy-5-(hydroxymethyl)tetrahydrofuran-2-yl)-6-hydrazinyl-7H-pyrrolo[2,3-d]pyrimidine-5-carboximidhydrazide having Formula IIIc (NSC #107512);

E) 4-amino-7-((2R,3R,4S,5R)-3,4-dihydroxy-5-(hydroxymethyl)tetrahydrofuran-2-yl)-6-hydrazinyl-7H-pyrrolo[2,3-d]pyrimidine-5-carboximidamide having Formula IIId (NSC #131663), F) 4-amino-7-((2R,3R,4S,5R)-3,4-dihydroxy-5-(hydroxymethyl)tetrahydrofuran-2-yl)-7H-pyrrolo[2,3-d]pyrimidine-5-carbothioamide (thiosangivamycin) having Formula IIIe (NSC #105827).

These bar graphs depict the dose-response of EGFP fluorescent signal in cells treated with a concentration range of compounds expressed as % of the solvent control signal. Reading each histogram from left to right the doses are, in decreasing concentration, 30 μM, 15 μM, 7.5 μM, 3.75 μM, 1.88 μM, 0.94 μM, and 0.46 μM respectively. All compounds revealed a dose-dependent reduction in EGFP fluorescence with Samples A, B and F showing the largest decrease in signal.

Figure 4:
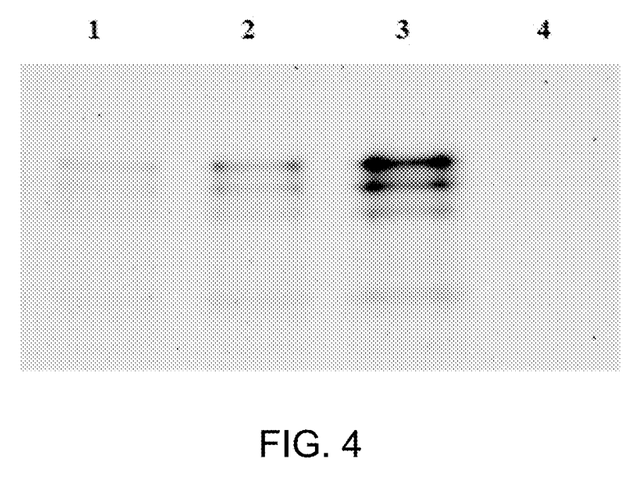
FIG. 4 lanes 1, 2 and 3 represent 3 µL, 6 µL and 12 µL of VLP isolated from wild type VP40 expressing cells.
Figure 5A:
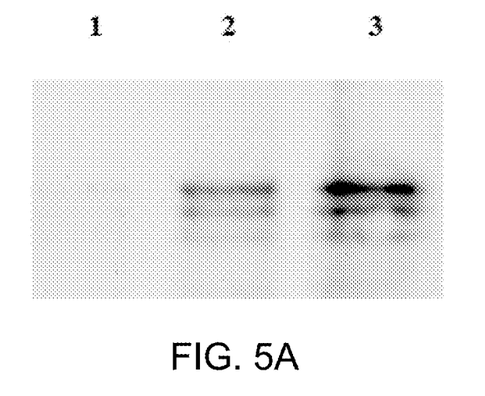
FIG. 5A-D depicts VLP isolated from A) DMSO control, B) 5 nM sangivamycin, C) 50 nM sangivamycin, and D) 500 nM sangivamycin with lanes 1, 2 and 3 again showing 3 µL, 6 µL and 12 µL of VLP.
Figure 5B:
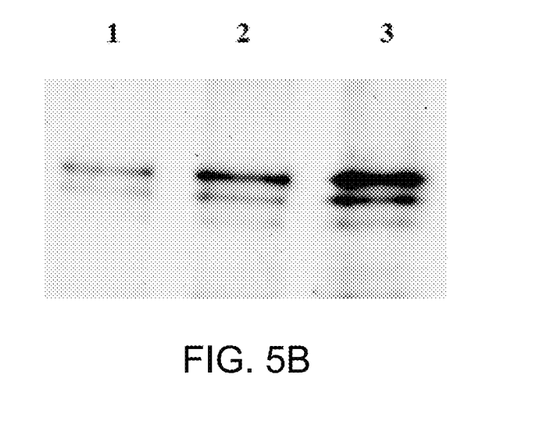
Figure 5C:
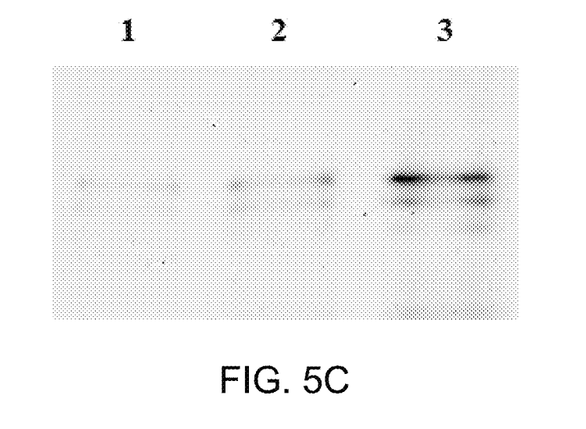
Figure 5D:
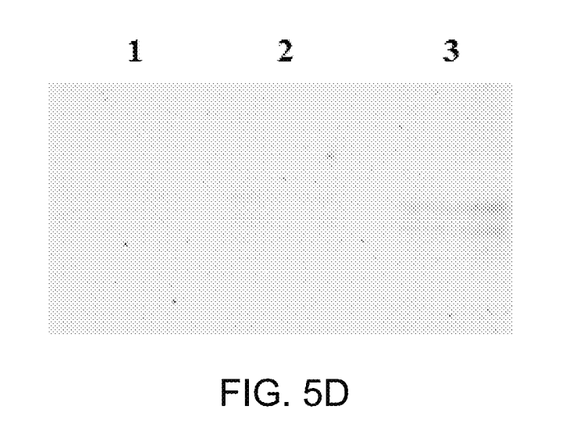

Another manner in which reduction in VLP formation was demonstrated was through the isolation of VLP in the cell culture by filtering the cell media through a 0.45 micron filter to isolate VLP from cell debris followed by a high speed (100,000×g) spin through a 20% sucrose cushion to isolate VLP from protein in the media. The isolated VLP were then re-suspended in gel loading buffer and run on an SDS-PAGE gel and western blotted for VP40 (V5-antibody was detected as a V5 tag located on the VP40 protein as a linker between EGFP and VP40). FIG. 4 lanes 1, 2 and 3 represent 3, 6 and 12 μL of VLP isolated from wild type VP40 expressing cells. FIG. 4 lane 4 represents 12 μL of VLP isolated from L117R VP40 expressing cells. VLP were detected at the lowest amount loaded for wild type (FIG. 4 lane 1), however, no signal was detected at the highest loading amount for L117R (FIG. 4 lane 4) which cannot form VLP. As in FIG. 4, FIG. 5 depicts VLP isolated from A) DMSO control, B) 5 nM sangivamycin, C) 50 nM sangivamycin, and D) 500 nM sangivamycin with lanes 1, 2 and 3 again showing 3, 6 and 12 μL of VLP. FIGS. 5A and 5B show similar amounts of VLP, while FIG. 5C shows a clear reduction in VLP at 50 nM sangivamycin. FIG. 5D shows a drastic reduction in VLP at 500 nM sangivamycin with VLP only faintly detected at 12 μL in lane 3.

The data depicted in FIGS. 1-4 indicate that sangivamycin and its analogs affect the ability of VP40 to form VLP, in the absence of other Ebola components. Because sangivamycin is a nucleoside analog, minigenome assays were performed to test the effect sangivamycin has on Ebola's L polymerase (i.e. the typical target of antiviral nucleoside analogs).

Table I summarizes a minigenome assay of sangivamycin and sangivamycin hydrochloride.

TABLE I

| Test Compound (15 μM) | % EGFP signal | % mCherry signal |
|---|---|---|
| sangivamycin | 27 | 4 |
| sangivamycin HCl | 20 | 10 |

A six plasmid minigenome expression system (GFP-7A editing site-mCherry, T7, NP, VP35, VP30, L) enables expression of both GFP and mCherry fluorescent reporters through the Ebola L polymerase requiring accessory viral proteins NP, VP35, VP30 for activity and T7 RNA polymerase to boost initial transcription. The results shown in Table I indicate that both GFP and mCherry expression were inhibited in the presence of 15 μM sangivamycin or sangivamycin HCl.

Figure 6:
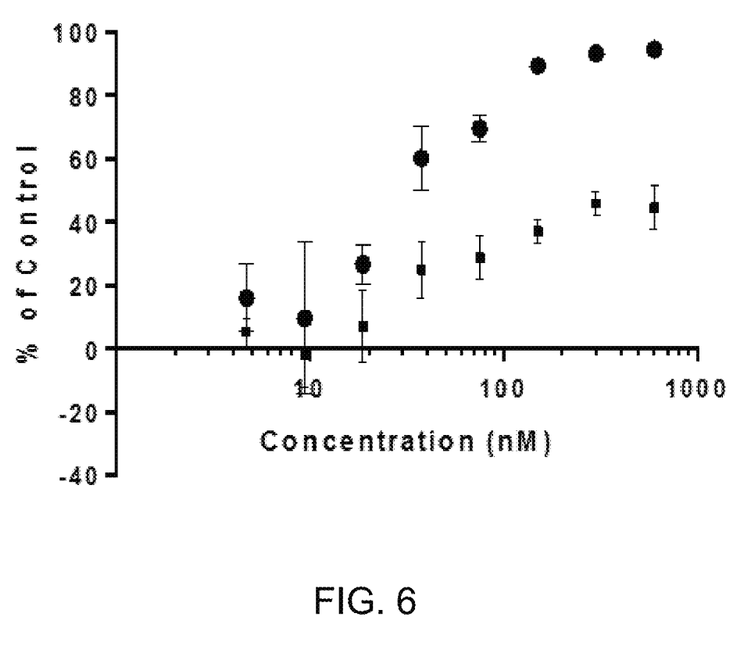
FIG. 6 depicts the percent inhibition (●) and percent cytotoxicity (■) of sangivamycin in a minigenome assay which measures inhibition of RNA transcription and replication through the Ebola L polymerase. A luciferase reporter was used to obtain % inhibition, whereas a tetrazolium salt-based cell viability assay (WST) was used to measure the relative cytotoxicity.

FIG. 6 indicates that sangivamycin inhibits RNA transcription and replication through the Ebola L polymerase in minigenome reporter systems. The data found in FIG. 6 are from a similar minigenome assay. The difference was that the GFP-7A editing site-mCherry reporter was replaced with a luciferase reporter. 293T Cells were treated in triplicate for 48 hours with doses ranging from 4.7-600 nM of sangivamycin. As evidenced in FIG. 6 there was a dose-dependent effect (50% inhibitory concentration ($IC_{50}$)=30 nM) (●). In addition, a tetrazolium salt-based cell viability assay (WST) was used to measure the relative cytotoxicity (■). In the WST assay, the tetrazolium compound was bio-reduced by cells to a colored formazan product by dehydrogenase enzymes in metabolically active cells thereby measuring cell viability. The data from Table I and FIG. 6 indicate sangivamycin affected both Ebola transcription through the L polymerase.

FIGS. 7A-7F are graphs summarizing cell-based antiviral assays. The percent inhibition that the test compounds displayed is indicated by (●), whereas the percent toxicity is indicated by (■). These assays were used to evaluate the antiviral capability of the disclosed compounds against a fully-functional Ebola virus. The strain of Ebola that was used in this assay was isolated from the Makon variant of Ebola (EBOV-Mak); the variant that was spread in the most recent outbreak of Ebola in Eastern Africa in 2014. The celltype infected was the immortalized human liver cell line, Huh7. Huh7 cells were plated at 30,000/well in black opaque or clear bottom 96-well Operetta plates one day prior assay. Sangivamycin was tested in an 8-point dose response curve with 2-fold dilutions. Each dose was run in triplicate. After 1 hour treatment, cells were infected with EBOV-Mak at a multiplicity of infection (MOI) of 0.5. At 24 hours or 48 hours post-inoculation, the plates were fixed with 10% neutral buffered formalin. Cells were stained with a corresponding primary antibody against each Ebola virus EBOV-VP40 (BMDO4B007 AE11) followed by a fluorescently conjugated secondary antibody. Cell fluorescence levels were measured using the Operetta High Content Imaging system and the levels correspond to the amount of viral infectivity. The experiments were run on duplicate plates on 2 separate days. Parallel mock-infected cells were treated with the disclosed compounds to determine cytotoxicity using the Cell Titer-Glo Luminescence Cell Viability Assay (Promega), which utilizes a luminescent reporter to measure ATP levels to assess cell viability. Signal-to-noise ratio and Z' factor scores were assessed as quality control parameters for each plate of each run.

Figure 7A:
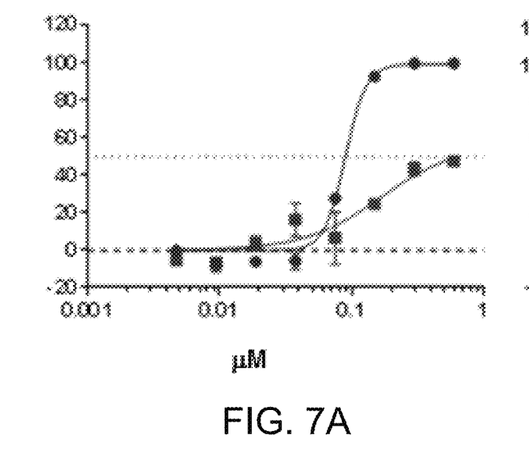
Figure 7B:
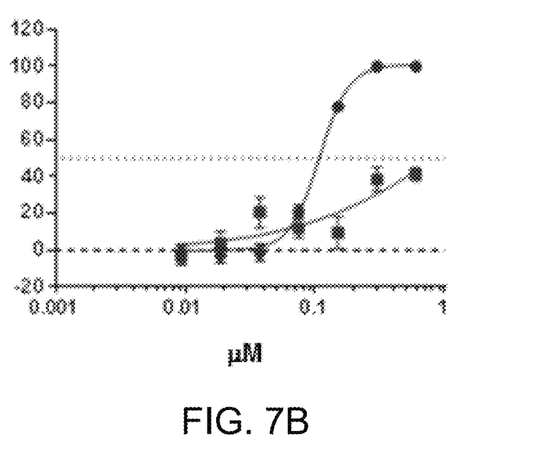
Figure 7C:
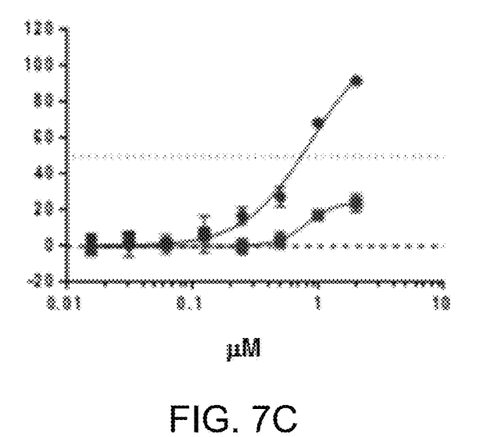
Figure 7D:
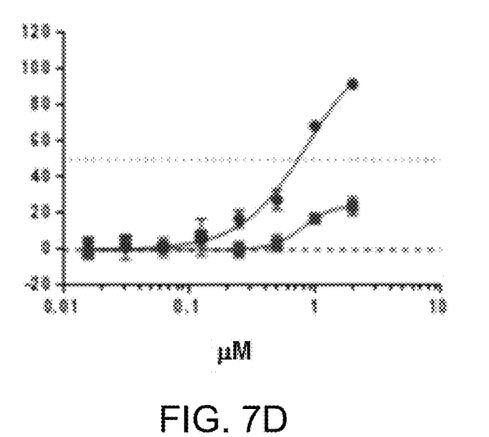
Figure 7E:
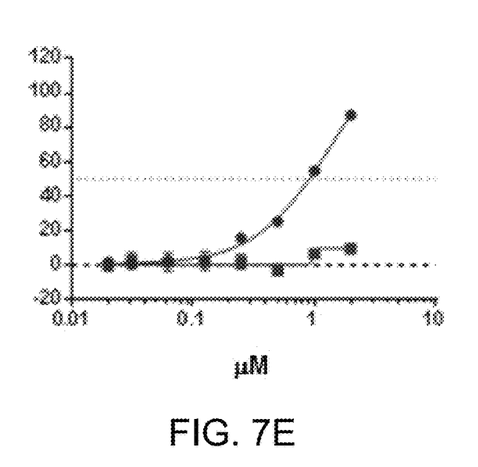
Figure 7F:
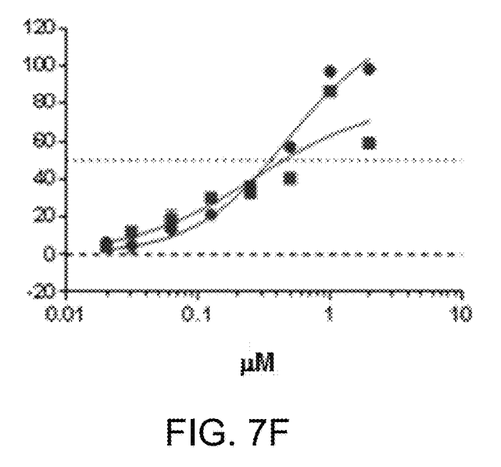

The data shown is FIG. 7A corresponds to sangivamycin, FIG. 7B corresponds to sangivamycin HCl, FIG. 7C corresponds to the compound having Formula IIIb, FIG. 7D corresponds to the compound having Formula IIIc, FIG. 7E corresponds to the compound having Formula IIId and FIG. 7F corresponds to thiosangivamycin.

FIG. 7 reveals that Ebola infectivity was inhibited by all analogs disclosed in FIG. 3. In addition, the effect each compound had on VP40, as shown in FIG. 3, corresponds well to the levels shown in FIGS. 7A-7F. These data indicate that sangivamycin and sangivamycin HCl had the greatest effect with $IC_{50}$ values of ~100 nM with the 50% cytotoxicity concentration not reached at the highest a concentration tested of 600 nM (dotted line on graphs represents the 50% IC or CC). Also, similar to FIG. 3 the compounds represented by Formulae IIIb-IIId were less effective than sangivamycin and sangivamycin HCl. Although thiosangivamycin displayed nanomolar inhibitory concentrations in the Huh7 assay, the cytotoxicity and inhibitory concentrations overlapped, suggesting that in the Huh7 assay, the inhibitory activity could not be separated from thiosangimamycin's cytotoxic activity.

Other advantages which are obvious and which are inherent to the disclosure will be evident to one skilled in the art. It will be understood that certain features and sub-combinations are of utility and may be employed without reference to other features and sub-combinations. This is contemplated by and is within the scope of the claims. Since many possible embodiments may be made of the disclosure without departing from the scope thereof, it is to be understood that all matter herein set forth or shown in the accompanying drawings is to be interpreted as illustrative and not in a limiting sense.

What is claimed is:

1. A method for preventing the spread of an Ebola virus infection, comprising contacting a subject at risk of developing an Ebola virus infection with a therapeutically effective amount of a compound having the formula:

wherein X is chosen from NH, O or S;
$R^1$ is chosen from —$NH_2$, —NHOH or —$NHNH_2$; and
$R^2$ is chosen from hydrogen or —$NHNH_2$; or
a pharmaceutically acceptable salt thereof; or
a mixture thereof;

wherein the compound inhibits the self-assembly of an Ebola VP40 protein; and wherein the therapeutically effective amount is from 1.0 mg/kg to about 10 mg/kg of the body mass of the subject.

2. The method according to claim 1, wherein the compound has the formula:

[Structure: pyrrolo[2,3-d]pyrimidine nucleoside with R¹, R², X substituents]

or a pharmaceutically acceptable salt thereof;
or a mixture thereof.

3. The method according to claim 1, wherein the compound is selected from:

a) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide (sangivamycin) having Formula IIIa:

[Structure: Formula IIIa]

or a pharmaceutically acceptable salt thereof;

b) 4-amino-7-((2R,3R,4S,5R)-3,4-dihydroxy-5-(hydroxymethyl)tetrahydrofuran-2-yl)-6-hydrazinyl-N-hydroxy-7H-pyrrolo[2,3-d]pyrimidine-5-carboximidamide having Formula IIIb:

[Structure: Formula IIIb]

or a pharmaceutically acceptable salt thereof;

c) 4-amino-7-((2R,3R,4S,5R)-3,4-dihydroxy-5-(hydroxymethyl)tetrahydrofuran-2-yl)-6-hydrazinyl-7H-pyrrolo[2,3-d]pyrimidine-5-carboximidhydrazide having Formula IIIc:

[Structure: Formula IIIc]

or a pharmaceutically acceptable salt thereof;

d) 4-amino-7-((2R,3R,4S,5R)-3,4-dihydroxy-5-(hydroxymethyl)tetrahydrofuran-2-yl)-6-hydrazinyl-7H-pyrrolo[2,3-d]pyrimidine-5-carboximidamide having Formula IIId:

[Structure: Formula IIId]

or a pharmaceutically acceptable salt thereof;

e) 4-amino-7-((2R,3R,4S,5R)-3,4-dihydroxy-5-(hydroxymethyl)tetrahydrofuran-2-yl)-7H-pyrrolo[2,3-d]pyrimidine-5-carbothioamide (thiosangivamycin) having Formula IIIe:

or a pharmaceutically acceptable salt thereof; or
f) mixtures thereof.

4. The method according to claim 1, wherein the compound is sangivamycin having the formula:

Formula IIIe or a pharmaceutically acceptable salt thereof.

* * * * *